US005686273A

United States Patent [19]
Eisenschink et al.

[11] Patent Number: 5,686,273
[45] Date of Patent: *Nov. 11, 1997

[54] FERMENTATION PROCESS FOR PRODUCING NATAMYCIN WITH ADDITIONAL CARBON AND NITROGEN

[75] Inventors: Michael Allen Eisenschink, Lisle, Ill.; James R. Millis, Kohler; Phillip Terry Olson, Manitowoc, both of Wis.

[73] Assignee: Cultor Food Science, Inc., New York, N.Y.

[*] Notice: The term of this patent shall not extend beyond the expiration date of Pat. No. 5,231,014.

[21] Appl. No.: 262,804

[22] Filed: Jun. 20, 1994

Related U.S. Application Data

[63] Continuation-in-part of Ser. No. 997,614, Dec. 23, 1992, abandoned, which is a continuation-in-part of Ser. No. 740,545, Aug. 5, 1991, abandoned, and a continuation-in-part of Ser. No. 997,613, Dec. 23, 1992, abandoned, which is a continuation-in-part of Ser. No. 740,536, Aug. 5, 1991, abandoned.

[51] Int. Cl.⁶ .................................................. C12P 17/18
[52] U.S. Cl. .......................... 435/119; 435/118; 435/76; 435/244
[58] Field of Search ........................ 435/76, 118, 119, 435/244

[56] References Cited

U.S. PATENT DOCUMENTS

| 3,015,612 | 1/1962 | Pirt et al. |
| 3,062,724 | 11/1962 | Reusser ................................ 435/76 |
| 3,378,441 | 4/1968 | Bridger et al. ........................ 435/76 |
| 4,167,450 | 9/1979 | Chesbro et al. ...................... 435/244 |
| 4,536,494 | 8/1985 | Carter ................................... 514/31 |
| 4,600,706 | 7/1986 | Carter ................................... 514/31 |
| 5,231,014 | 7/1993 | Eisenschink et al. ................ 435/76 |

FOREIGN PATENT DOCUMENTS

| 0218265 | 9/1957 | Australia . |
| 669761 | 9/1963 | Canada . |
| 677040 | 12/1963 | Canada . |
| 684259 | 4/1964 | Canada . |
| 359517 | 3/1957 | Sweden . |
| 846933 | 7/1957 | United Kingdom . |
| 0844289 | 8/1960 | United Kingdom . |
| 2106498 | 7/1982 | United Kingdom . |
| 8400777 | 3/1984 | WIPO . |

OTHER PUBLICATIONS

Creuger, et al., On: Biotechnology, A Textbook of Industrial Microbiology, *Sinauer Associates, Inc.*, 258–261, 1990.
Omura, et al., Macrolide Antibiotics, *Biotechnology*, 4, 386–387, 1986.
Onken, et al., Control and Optimization, *Biotechnology*, 2, 792, 1985.

*Primary Examiner*—Irene Marx
*Attorney, Agent, or Firm*—Ronald S. Courtney, Esq.

[57] ABSTRACT

An improved method for producing natamycin by fermentation is disclosed. In the method, which comprises, in order, the steps of:

(a) introducing an inoculum of a natamycin producing *Streptomyces species* to a fermentation medium to produce a fermentation broth comprising the fermentation medium and inoculum; and (b) producing natamycin by fermentation in the fermentation broth;

the improvement comprising:

(1) providing at least 15 g/L of a protein nitrogen source to the fermentation medium; wherein the protein nitrogen source comprises a non-yeast protein component and a yeast protein component, and the ratio of non-yeast nitrogen component to yeast protein component being from about 3:1 to 9:1, based on the protein content of the source;

(2) providing a carbon source to the fermentation medium at from about 80 g/L to 250 g/L; wherein the carbon source addition is carried out during step (b) so as to maintain a concentration of carbon source of from about 5 g/L to 30 g/L; and (3) continuing the fermentation until the fermentation broth comprises at least 5 g/L natamycin.

16 Claims, 3 Drawing Sheets

FERMENTATION PROCESS FOR PRODUCING NATAMYCIN WITH ADDITIONAL CARBON AND NITROGEN

CROSS-REFERENCE TO RELATED APPLICATIONS

This application is a continuation-in-part of U.S. patent application 07/997,614, filed Dec. 23, 1992, now abandoned, which was a continuation-in-part of U.S. application 07/740,545, filed Aug. 5, 1991, now abandoned, and a continuation-in-part of U.S. patent application 07/997,613, filed Dec. 23, 1992, now abandoned, which was a continuation-in-part of U.S. application 07/740,536, filed Aug. 5, 1991, now abandoned, all of which are incorporated herein by reference.

FIELD OF THE INVENTION

The invention relates to a method for producing natamycin. In particular, this invention is a process for producing natamycin by fermentation in a broth that comprises a non-yeast protein component and a yeast protein component.

BACKGROUND OF THE INVENTION

Natamycin (also known as pimaricin or tenecetin) is a member of the polyene family of antimycotics (Florey, "Analytical Profiles of Drug Substances", Vol. 10, 1981; Merck Index, 8th ed., "Pimaricin", p. 834). The compound is a tetraene with a molecular weight of about 666, empirical formula corresponding generally to $C_{33}H_{47}NO_{13}$, and it contains a glycosidically-linked carbohydrate moiety, mycosamine. Natamycin has an isoelectric point of about pH 6.5.

Fermentation processes for producing natamycin are described in: Koninklijke Netherlandsche Gist- & Spiritusfabriek, U.K. Patent 844,289; American Cyanamid, U.K. Patent 846,933; Backus, Canadian Patent 677,040; and Struyk, Australian Patent 218,265 and Canadian Patent 669,761. Although its valuable antibiotic and antifungal properties have been recognized, there has been little research or commercialization of natamycin because of the extremely high cost of its manufacture. A need exists for method for producing useful quantities of natamycin in a cost effective manner.

SUMMARY OF THE INVENTION

The invention is an improved method for producing natamycin by fermentation. In the method, comprising, in order, the steps of:

(a) introducing an inoculum of a natamycin producing *Streptomyces* species to a fermentation medium to produce a fermentation broth comprising the fermentation medium and inoculum; and (b) producing natamycin by fermentation in the fermentation broth;

the improvement comprising:

(1) providing at least 15 g/L of a protein nitrogen source to the fermentation medium; wherein the protein nitrogen source comprises a non-yeast protein component and a yeast protein component, and the ratio of non-yeast nitrogen component to yeast protein component being from about 3:1 to 9:1, based on the protein content of the source;

(2) providing a carbon source to the fermentation medium at from about 80 g/L to 250 g/L; wherein the carbon source addition is carried out during step (b) so as to maintain a concentration of carbon source of from about 5 g/L to 30 g/L; and (3) continuing the fermentation until the fermentation broth comprises at least 5 g/L natamycin.

In a preferred embodiment the fermentation is continued until the fermentation broth comprises at least 10 g/L natamycin. In another preferred embodiment production medium is added and broth withdrawn during fermentation so that natamycin is produced in a continuous process.

DETAILED DESCRIPTION OF THE INVENTION

Spore Suspension

Figure 1:
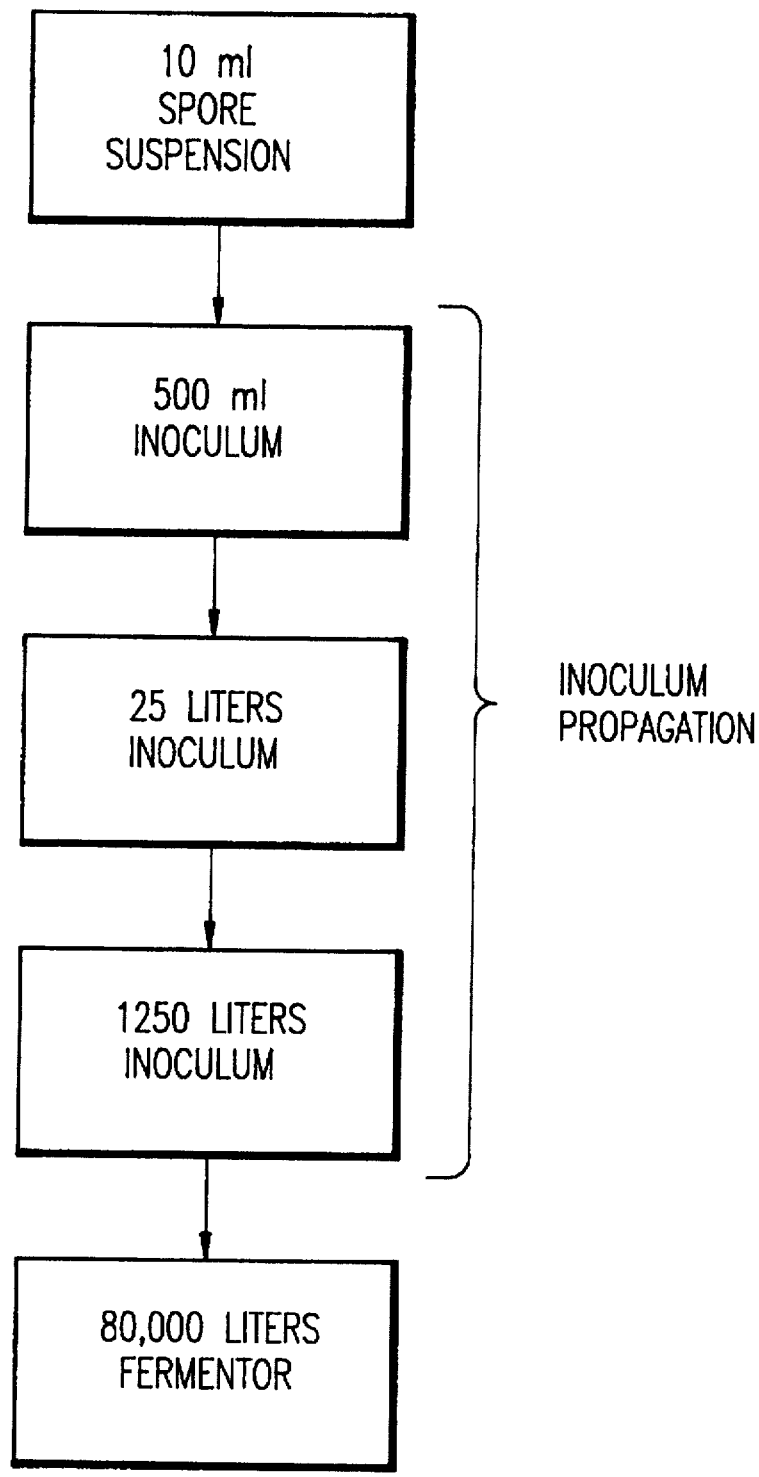
FIG. 1 is a schematic of the method for inoculum propagation.

Any natamycin producing *Streptomyces* species can be used in the method. A preferred *Streptomyces* species is *Streptomyces gilvosporeus*. A preferred strain of *Streptomyces gilvosporeus* has been deposited with the American Type Culture Collection (ATCC), 12301 Parklawn Drive, Rockville, Md. 20852, USA, and assigned registration No. 13326.

Spores of the natamycin producing organism are germinated to produce an actively growing culture. A sterilized (e.g., autoclaved), agar slant is heavily inoculated with the actively growing culture and incubated until the slant is substantially covered with spores. The spores are scraped into a small amount of a liquid, such as distilled water, nutrient medium, etc., to produce an aqueous spore suspension.

A number of agar slant media can be used to promote sporulation of the culture. Appropriate agar slant media typically comprise at least one of: yeast malt agar, Hickey-Turner agar, GYA agar, Pridham agar, potato dextrose, Bennett's agar, etc. Suitable media are given in the Examples.

The spore suspension typically contains about $10^5$–$10^{10}$ CFU/mL. A high concentration (e.g., $10^8$ CFU/mL or higher), of viable spores within the spore suspension is preferred. If the concentration of spores is too low, it takes much longer to produce the cell concentration required for cost-effective natamycin production. A lower spore concentration lengthens the propagation time and increases the likelihood of contamination by an unwanted organism. In addition, a low spore concentration may tend to promote the formation of large, tightly packed mycelial pellets. These pellets are unsuitable for obtaining high yields of natamycin due to problems associated with oxygen transfer, mass transfer of nutrients into the pellets, etc. Should the size of mycelial pellets become undesirable, the pellets can be broken apart physically, such as by using a shear force (e.g., blending).

Inoculum Propagation

The aqueous spore suspension is germinated and cell growth continued until the cell density is adequate to be used as an inoculum. A suitable inoculum cell density is about 1–5 g/L (dry weight). The inoculum is used at a volume of about 0.1–10% of the natamycin production medium volume.

The medium used for propagation determines the cell density and the metabolic state of the inoculum. A sufficient amount of protein nitrogen that contains complex growth factors (e.g., vitamins), inorganic elements (e.g., potassium, sodium, calcium, etc.), and trace elements (e.g., boron, cobalt, iron, copper, zinc, etc.) that are commonly present in the protein nitrogen source is needed to produce an inoculum possessing the desired cell density and metabolic state. The protein nitrogen source may be any source that will propagate the spore suspension into an inoculum that will produce the desired high yields of natamycin.

A source of metabolizable carbon must also be supplied to the medium in an amount sufficient to achieve the desired cell density. For best results, the carbon source should not be completely depleted during propagation. Depletion of the carbon source tends to adversely alter the metabolic state of the inoculum and reduce the yield of natamycin during fermentation.

A suitable medium for inoculum propagation may be prepared in water (e.g., low mineral content water, distilled water, etc.), and comprises: (a) about 2–16 g/L, typically about 8 g/L, of a protein nitrogen source; and (b) a sufficient metabolizable carbon source to avoid total carbon depletion, usually about 5–30 g/L, typically about 15 g/L. Suitable media are given in the Examples.

The medium may be prepared by conventional techniques (e.g., separate or simultaneous sterilization of the carbon and nitrogen sources at temperatures of about 120°–140° C.). After sterilization, the medium desirably has a pH of about 7. The spore suspension is introduced to the medium and the medium is heated to about 25°–40° C., typically, about 28°–35° C.

To achieve the large volumes of aqueous inoculum which are desirable for fermentation production of natamycin, several propagation steps are required, each carried out in a volume greater than the previous step. It is advantageous to keep the culture in an exponential growth mode during propagation by increasing the volume of the inoculum during each step of the propagation. This can be done by either minimizing the duration of each step or by minimizing the number of steps. Once the desired cell density has been achieved, the inoculum is transferred to a larger vessel for further growth. This process is illustrated by FIG. 1. The length of time an individual step is permitted to continue depends upon the composition of the medium, quantity of Streptomyces cells desired, temperature, etc. Typically, a propagation step continues for about 6 to 24 hours.

Propagation requires aeration of the inoculum. The vessel or flask housing the inoculum, may be agitated on a rotary shaker at about 200 rpm. or by impeller located within the vessel that houses the inoculum while sterile air is forced into the bottom of the vessel.

Natamycin Production

The fermentation medium must contain the proper amounts of metabolizable carbon and protein nitrogen. Also, it is desirable that the medium contain complex growth factors (e.g., vitamins), and inorganic elements (e.g., potassium, sodium, calcium, etc.), and trace elements (e.g., boron, cobalt, iron, copper, zinc, etc.), that are commonly present in the protein nitrogen source.

A suitable medium for fermentation may be prepared in water (e.g., low mineral content tap water, distilled water, etc.), and comprises: (a) about 80–250 g/L of a metabolizable carbon source; and (b) at least 15 g/L and, normally about 20–80 g/L, of a protein nitrogen source containing a high level of protein and trace ingredients. The protein nitrogen source comprises a non-yeast protein nitrogen component and a yeast protein nitrogen component. These two protein nitrogen components are present in a ratio ranging, respectively, from about 3:1 to 9:1 based on protein content of the components, preferably about 4:1 to 8:1 and more preferably about 5:1 to 7:1.

The non-yeast protein nitrogen component may be supplied from a wide range of sources, such as soy protein products (e.g., isolates, flours, meals, etc.). Desirable natamycin yields are obtained with a soy protein source comprising 80–95% protein. The non-yeast protein nitrogen component may also comprise beef extract, protein hydrolysates (e.g., peptones). The yeast nitrogen component is supplied by yeast protein (e.g., extracts, autolysates, etc.).

The production medium must also include a source of metabolizable carbon. The carbon source may be supplied in any expedient form such as glucose, polysaccharide, corn and potato starches, etc.

It is not necessary to initially add the entire mount of carbon source. An appropriate amount of carbon source may be initially added to the fermentation medium and addition continued after the fermentation has begun. For example, the initial concentration of carbon source may be about 40 g/L. Thereafter, carbon source is added to the fermentor at a rate that will maintain the concentration at or above the minimum level required for fermentation. Typically the concentration is maintained at about 5–30 g/L, more typically about 20 g/L. Toward the end of the fermentation, and after the major fermentation period, carbon source addition is discontinued so that little or no carbon source is left at the end of the fermentation.

The fermentation is carried out in an appropriately sized fermentation vessel. About 0.1–10%, usually about 2%, by volume of inoculum is added to the production medium. The remainder of the volume of the fermentor comprises the fermentation medium. Any technique for introducing the inoculum that delivers the inoculum in an active metabolic state and does not cause contamination of the culture is acceptable. To control foaming it may be desirable to add to the medium 0.01–1% by volume of an anti-foaming agent (e.g., a silicone defoamer).

The fermentation medium is brought to a temperature of about 25°–40° C., and normally 28°–35° C. The length of time which the fermentation process is allowed to continue depends upon the composition of the fermentation medium, temperature, quantity of cells in the inoculum, quantity of natamycin desired, etc. Typically, the fermentation process is conducted for about 70 to 168 hours.

Oxygen is supplied to the medium during fermentation. It is advantageous to maintain a dissolved oxygen level in the medium of about 20–80% of air saturation during the major portion of the fermentation. The ability to achieve a suitable dissolved oxygen level may be enhanced by proper coordination of the aeration and/or agitation rate. For example, the medium is aerated by forcing sterile air through the medium, usually at a rate of about 0.3–1.0 volumes of air per volume of medium. Although it is generally desirable to agitate the medium during aeration, aeration may produce the desired agitation.

Figure 2:
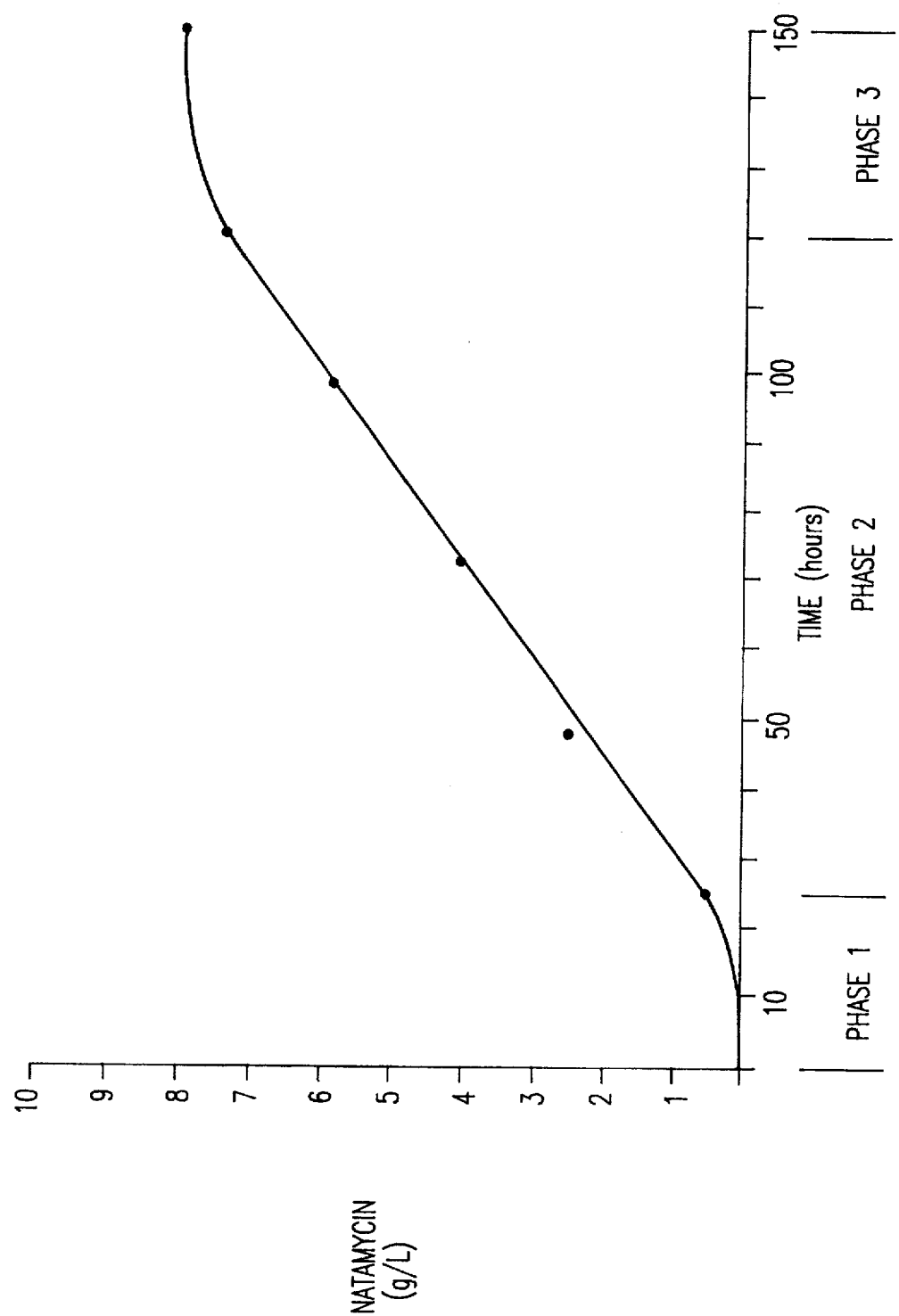
FIG. 2 shows the three phases that occur during batch fermentation.

Referring to FIG. 2, the relationship between time and natamycin concentration is shown for each of the three phases of the process. To ascertain the phase of fermentation the concentration of natamycin may be analyzed as a function of time. During the first phase the concentration of natamycin increases generally exponentially. The first phase includes the major portion of cell growth. During the second phase the concentration of natamycin increases linearly with time. Carbon source is added at a rate that will maintain carbon source concentration above the minimum level required for fermentation, typically at or near the rate at which carbon source is being consumed. The third phase is characterized by a plateau in natamycin concentration. In order to maximize the overall quantity of natamycin that is produced, it is desirable to use a medium and/or an environment that induces the second phase to be rapidly reached and maintained.

Initially the pH of the production medium is about 7.0. During fermentation the pH slowly decreases to about 4.5. Depending upon the end-use of the fermentation broth, a lowered pH may be desirable since the fermentation broth is more readily processed. At a pH of about 7 the fermentation broth may become relatively viscous, and recovery of natamycin may be more difficult. For natamycin recovery using the process described in U.S. patent application 08/237,437, filed May 3, 1994, a pH of about 4.5, is desirable. If a higher pH is desired, the pH by be controlled by addition of a pH control agent during fermentation. This process is described by Eisenschink, U.S. Pat. No. 5,231,014.

Continuous Process

Figure 3:
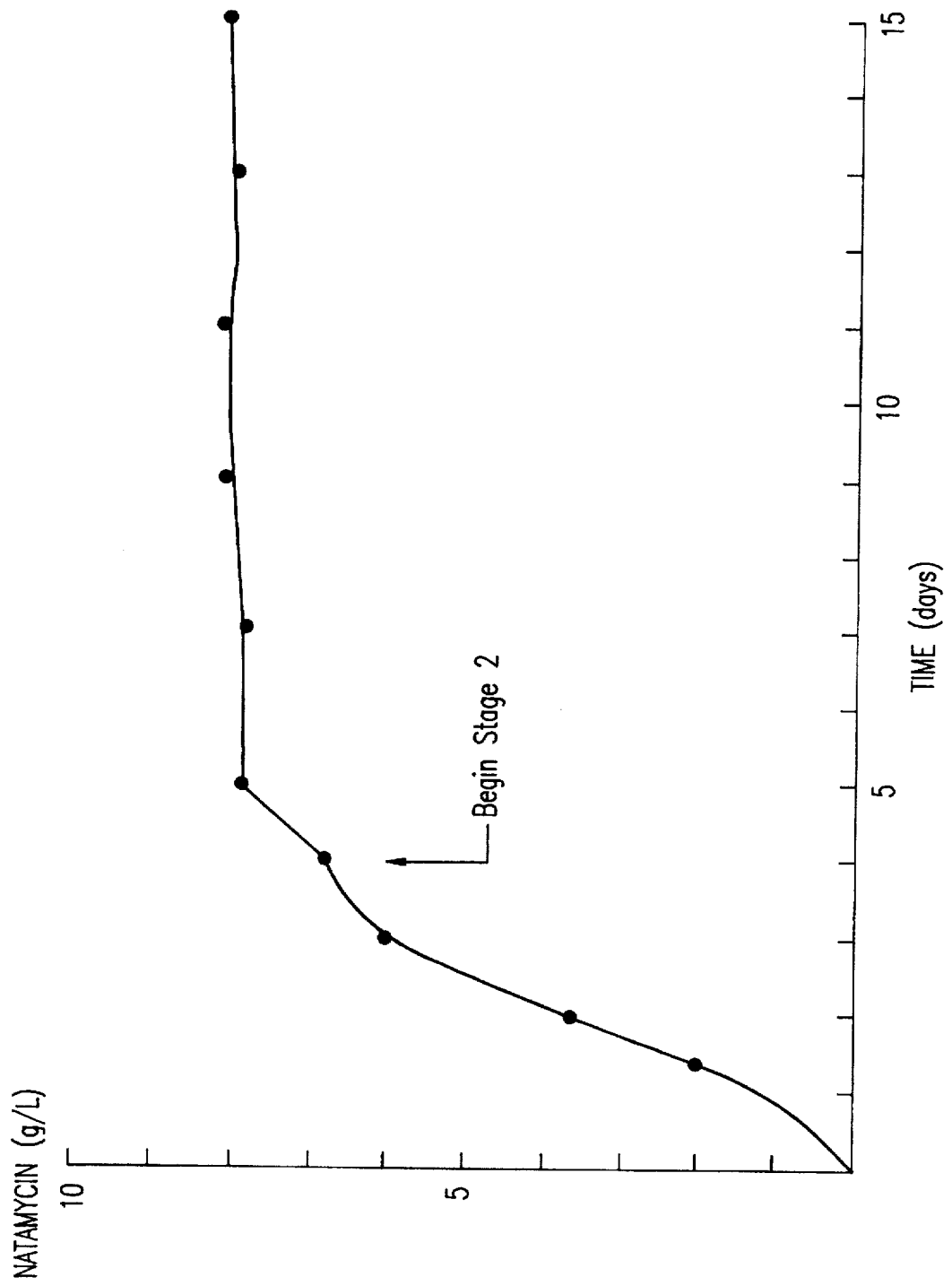
FIG. 3 shows the stages of the continuous process.

The continuous process comprises two stages. Referring to FIG. 3, in the first stage an inoculum is added to the production medium and grown to form a broth. As described above and shown in FIG. 2, the natamycin production rate increases from zero to a steady state and then begins to decline. During the second, or continuous production, stage, natamycin production occurs at a steady rate. Natamycin production is maintained by the continuous addition of production medium and removal of fermentation broth so that both the volume of fermentation broth in the fermentor and the concentration of natamycin in the fermentation broth remain essentially constant. Only production medium is added; no new inoculum is added during this stage.

The production rate may be adjusted by control of the medium composition and addition rate. Addition and removal may be carried out by any convenient technique, such as using a pump, pressure, gravity, etc. Depending on the medium and the equipment costs, it may be desirable to add medium and remove broth at a somewhat faster rate than that which will produce maximum possible medium utilization and maximum natamycin concentration. A natamycin concentration of 7.0–9.0 g/L may be appropriate. Also, depending on the type of equipment being used, in may be desirable to add medium and/or remove broth intermittently as long as the average broth volume remains essentially constant. If desired, during the second stage the composition of the medium can be adjusted or even significantly changed to optimize natamycin production.

While, in theory, the continuous phase can continue indefinitely, in practice, this phase is limited by the contamination of the production medium with other cultures and by equipment malfunction. However, continuous production may be continued for at least 40 days or until natamycin production decreases to an uneconomical level.

Natamycin Recovery

The natamycin is recovered from the broth. In the process disclosed in U.K. Patent 846,933, natamycin is recovered by methanol extraction followed by adsorption and elution. Penick, U.S. Pat. No. 3,378,441, discloses recovery of natamycin by salting it out of the fermentation broth, extracting with methanol, removing the solids, and then evaporating the liquid. Struyk, U.S. Pat. No. 3,892,850, discloses recovery of natamycin by extraction with acidified butanol followed by distillation and precipitation. Struyk also discloses calcium chloride dissolved in methanol to improve natamycin solubility. U.K. Patent No. 844,289 shows the precipitation of natamycin from acetic acid by the addition of water. U.S. patent application 08/237,437, filed May 3, 1994, incorporated herein by reference, discloses improved methods of natamycin recovery. In one process methanol is added, the pH adjusted to 1.0 to 4.5, solids removed, the pH raised to 6.0–9.0 and the precipitated natamycin recovered.

INDUSTRIAL APPLICABILITY

The invention produces fermentation broth containing at least 5 g/L, typically 7–12 g/L, of natamycin. This high concentration improves recovery from the broth and makes the production process more economically attractive. Natamycin can be used as an anti-fungal additive for animal feed (see Carter, U.S. Pat. Nos. 4,536,494 and 4,600,706).

The invention is illustrated by reference to the following examples which illustrate, but not limit, the invention. Unless specified otherwise, commercially available reagent grade materials were used.

EXAMPLES GLOSSARY

| GLOSSARY | |
| --- | --- |
| Profam ® S970 | Isolated soy protein, contains a minimum of 90% protein; Grain Processing Corp., Muscatine, IA |
| Flav-R-Base ™ Type KAT | Primary autolyzed yeast extract, contains about 70% protein; Stauffer Chemical, Westport, CT |

MEDIA

Media were prepared in distilled water and sterilized at 121° C. for about 0.25 hr before use. The following media were prepared:

Sporulation Medium 1

4 g/L yeast extract (Difco "Bacto" Yeast Extract); 10 g/L malt extract (Difco Malt Extract); 4 g/L glucose; and 20 g/L agar.

Sporulation Medium 2

3 g/L yeast extract (Difco "Bacto" Yeast Extract); 3 g/L malt extract (Difco Malt Extract); 5 g/L peptone (Difco "Bacto" peptone); 10 g/L glucose; and 15 g/L agar.

Inoculum Medium 1

15 g/L glucose; 10 g/L sodium chloride; and 10 g/L peptone (Hormel PSR5 peptone).

Inoculum Medium 2

20 g/L glucose; 10 g/L sodium chloride; 6 g/L corn steep liquor (PPM (brand), Corn Steep Liquid); and 6 g/L peptone (Difco "Bacto" peptone).

EXAMPLES 1–4

These examples illustrate production of natamycin by *Streptomyces gilvosporeus* on a medium containing a non-yeast nitrogen component and a yeast nitrogen component in the ratio of about 5.6:1, based on protein content.

Sporulation

*Streptomyces gilvosporeus*, ATCC 13326, was obtained from the American Type Culture Collection as a freeze-dried spore suspension and used as the culture source. The culture was held on the agar slants (Sporulation Medium 1) at about 25° C. until the culture sporulated. The culture sporulated heavily within about 10 days and was used after 14 days.

Spores were scraped off these agar slants into a small amount of inoculum medium (Inoculum Medium 1) so that the spore concentration in the resulting spore suspension was about $10^8$ CFU/mL. Glycerol was added to make the suspension 10% glycerol (volume/volume). The resulting suspension was stored at −80° C. until needed.

Inoculum Propagation

About 1.5 mL of the spore suspension was added to 100 mL of inoculum medium (Inoculum Medium 1) in a 500 mL baffled flask. The inoculum in the baffled flask was incubated for 12 hr at 29° C. and agitated at about 200 rpm on a rotary shaker. About 2 mL of the resulting culture was transferred to 100 mL of inoculum medium and incubation repeated for another 12 hr. About 2 mL of this culture was transferred to 200 mL of medium in a 1 L baffled flask and the incubation repeated for another 24 hr. This culture was used to inoculate 8 L of production medium.

Fermentation

The production medium was prepared in distilled water in a 14 L fermentor and the pH was adjusted to about 7.6 with potassium hydroxide. The fermentor was then sterilized for about 15 min at about 121° C. Glucose was sterilized separately as a 60% solution in distilled water. The composition of the production medium is given in Table 1. The medium also contained 0.05 mL/L defoamer (Mazu, DF 289).

Before inoculation, the production medium was heated to about 29° C. and glucose solution was added to produce an initial glucose concentration of about 40 g/L. An aeration rate of about 0.3 v/v-min. (volumes of air per volume of medium per minute) and an agitation rate of about 300 rpm was established for the fermentor.

Inoculum was added to the fermentation vessel until the medium in the fermentation vessel was about 2% by volume inoculum. After about 40 hr of fermentation, glucose was added at about 1–2 g/L-hr to maintain a glucose concentration of about 20 g/L in the fermentation vessel. The agitation rate was increased as necessary to maintain a dissolved oxygen level of about 50% of air saturation.

An initial volume of about 8.0 L production medium was fermented for about 120 hr. Glucose was added as necessary to maintain natamycin production. Up to 230 g/L of glucose was added (Example 4). Natamycin production is indicated in Table 1.

TABLE 1

| Example | Soy Protein[a] (g/L) | Yeast Extract[b] (g/L) | Ratio[c] | Natamycin[d] (g/L) | Natamycin[e] (g/L) |
|---|---|---|---|---|---|
| 1 | 19.5 | 4.5 | 5.6 | 8.1 | 9.3 |
| 2 | 26.0 | 6.0 | 5.6 | 10.0 | 11.4 |
| 3 | 32.5 | 7.5 | 5.6 | 12.9 | 15.3 |
| 4 | 39.0 | 9.0 | 5.6 | 15.2 | 18.8 |

[a]Profam ® S970 (minimum of 90% protein)
[b]Flav-R-Base ™ Type KAT (about 70% protein)
[c]Ratio of non-yeast protein to yeast protein corrected for protein content of the extracts.
[d]Measured concentration.
[e]Corrected to the original volume to compensate for varying amounts of glucose solution added during fermentation.

EXAMPLES 5–8

These examples illustrate natamycin production with different ratios non-yeast protein to yeast protein.

Sporulation

*Streptomyces gilvosporeus*, ATCC 13326, was held on the agar slants (Sporulation Medium 2) at about 25° C. until the culture sporulated. The culture sporulated heavily within about 10 days and was used after 15 days.

Spores were scraped off these agar slants into a small amount of inoculum medium (Inoculum Medium 2) so that the spore concentration in the resulting spore suspension was about $10^8$ CFU/mL. The resulting suspension was used immediately after preparation.

Inoculum Propagation

About 2 mL of the spore suspension was added to 100 mL of inoculum medium (Inoculum Medium 2) in a 500 mL baffled flask. The culture was incubated for 48 hr at 29° C. and agitated at about 200 rpm on a rotary shaker. This culture (20 mL) was used to inoculate 700 mL of production medium.

Fermentation

Fermentation was carried out as described in Examples 1–4, except that fermentation was carded out in 700 mL of production medium in a 1 L fermentor using the production media given in Table 2. Natamycin production is indicated in Table 2.

TABLE 2

| Example | Soy Protein[a] (g/L) | Yeast Extract[b] (g/L) | Ratio[c] | Natamycin[d] (g/L) |
|---|---|---|---|---|
| 5 | 13.0 | 4.5 | 3.7 | 5.9 |
| 6 | 18.0 | 4.5 | 5.1 | 9.0 |
| 7 | 13.0 | 3.0 | 5.6 | 7.6 |
| 8 | 18.0 | 3.0 | 7.7 | 4.5 |

[a]Profam ® S970 (minimum of 90% protein)
[b]Flav-R-Base ™ Type KAT (about 70% protein)
[c]Ratio of non-yeast protein to yeast protein corrected for protein content of the extracts.
[d]Measured concentration.

EXAMPLE 9

This example illustrates natamycin production without addition of additional glucose and on a medium containing a non-yeast nitrogen component and a yeast nitrogen component in the ratio of about 1:1, based on protein content. The procedure of Example 1 of American Cyanamid, U.K. Patent 846,933, was followed.

The procedure of Examples 1–4 was followed with the following exceptions: (1) the fermentation medium contained about 10 g/L glucose, 2 g/L beef extract, 2 g/L Batco yeast extract, 0.5 g/L asparagine and 0.5 g/L dibasic potassium phosphate and (2) no glucose was added subsequently. After about 72 hr of fermentation, the concentration of natamycin was about 0.75 g/L.

EXAMPLE 10

This example illustrates continuous production of natamycin on a medium containing a non-yeast nitrogen component and a yeast nitrogen component in the ratio of about 5.6:1, based on protein content of the components.

Sporulation and Inoculum Propagation

The procedure of Examples 5–8 was followed.

First Stage

The first stage natamycin production medium had the following initial composition: 19.5 g/L soy protein isolate (ADM, "Profam" S970); 4.5 g/L yeast extract (Stauffer, Type KAT); and 0.05 mL/L defoamer (Mazu, DF 289)

About 600 mL of medium was prepared in distilled water in a 1 L fermenter. The pH was adjusted to about 7.6 with potassium hydroxide. The fermenter was sterilized for about 0.25 hr at about 121° C. A 50% glucose solution was sterilized separately and about 40 g/L added to the medium. The medium was heated to about 29° C. The aeration rate was set at about 250 mL/min and the agitation rate at 500 rpm.

The inoculum was added to the fermentation vessel until the fermentation vessel had an inoculum content of about 2% by volume. Glucose was added to the medium in the fermentor after about 40 hr of fermentation to maintain a glucose concentration of about 20 g/L glucose in the fermentation vessel. Glucose was fed to the vessel at about 1 g/L-hr. The agitation rate of the fermentation vessel was increased as necessary to maintain a dissolved oxygen level of about 20% of air saturation.

Second Stage

About 72 hr after inoculation, the natamycin production rate began to decline. The natamycin concentration in the broth was about 3.9 g/L. Second stage medium was added and the fermentation broth was withdrawn from the fermenter at a rate of about 12 mL/hr to maintain a constant broth volume of about 600 mL. The second stage medium contained about 19.5 g/L soy protein isolate, 4.5 g/L yeast extract, 50 g/L glucose and 0.2 mL/L of defoamer.

Addition and withdrawal was continued at about 12 mL/hr, and the fermentation continued until about 200 hr after the start of the first fermentation stage. The natamycin concentration was 4.5 g/L. The product was recovered from the withdrawn broth.

The medium was changed to: 26 g/L soy protein isolate, 6 g/L yeast extract, 80 g/L glucose and 0.3 mL/L of defoamer. Addition of nutrient medium and withdrawal of broth were continued at the same rate. At about 250 hr from the start, the concentration of natamycin in the broth had increased to 8.5 g/L. The concentration remained approximately constant for the rest of the fermentation. Fermentation was discontinued at about 450 hr.

EXAMPLE 11

This example illustrates continuous production of natamycin on a medium containing a non-yeast nitrogen component and a yeast nitrogen component in the ratio of about 5.6:1, based on protein content.

The general procedure of Example 10 was followed except that the production medium contained 26 g/L soy protein isolate, 6 g/L yeast extract, and 0.3 mL/L of defoamer and the volume of fermentation medium was about 3 L. After about 70 hr, the natamycin concentration was 6.0 g/L. Addition of medium and withdrawal of broth was begun. The added medium contained about 26 g/L soy protein isolate, 6 g/L yeast extract, 80 g/L glucose and 0.3 mL/L of defoamer. Second stage medium was added and the fermentation broth was withdrawn from the fermenter at a rate of about 1.5 L/day to maintain a constant broth volume of about 3 L. At about 117 hr a steady state natamycin concentration of about 8.0 g/L was attained. Fermentation was continued for about 250 hr.

What is claimed is:

1. In a method for producing natamycin, comprising, in order, the steps of:
    (a) introducing an inoculum of a natamycin producing Streptomyces strain to a fermentation medium to produce a fermentation broth comprising the fermentation medium and inoculum; and
    (b) producing natamycin by culturing the Streptomyces strain in the fermentation broth; the improvement comprising:
    (1) providing at least about 15 g/L of a protein nitrogen source to the fermentation medium; wherein the protein nitrogen source comprises a non-yeast protein component and a yeast protein component, and the ratio of non-yeast protein component to yeast protein component being from about 3:1 to 9:1, based on the protein content of the source;
    (2) providing a carbon source to the fermentation medium at from about 80 g/L to 250 g/L; wherein the carbon source addition is carried out during step (b) so as to maintain a concentration of carbon source of from about 5 g/L to 30 g/L;
    (3) continuing the fermentation until the fermentation broth comprises at least 5 g/L natamycin; and
    (4) recovering the natamycin from the fermentation broth.

2. The method of claim 1, wherein said natamycin producing Streptomyces strain has all the identifying characteristics of Streptomyces gilvosporeus ATCC 13326, and in which the fermentation is continued until the fermentation broth comprises at least 10 g/L natamycin.

3. The method of claim 1 in which the natamycin producing Streptomyces strain is Streptomyces gilvosporeus.

4. The method of claim 1 in which the ratio of non-yeast protein component to yeast protein component is 4:1 to 8:1.

5. The method of claim 1 in which, in step (4), methanol is added, the pH adjusted to 1.0 to 4.5, solids removed, the pH raised to 6.0–9.0 and precipitated natamycin recovered.

6. The method of claim 5 in which the natamycin producing Streptomyces strain has all the identifying characteristics of Streptomyces gilvosporeus ATCC 13326, the fermentation is continued until the fermentation broth comprises at least 10 g/L natamycin, and the ratio of non-yeast protein component to yeast protein component is 4:1 to 8:1.

7. The method of claim 5 in which the natamycin producing Streptomyces strain is Streptomyces gilvosporeus, the fermentation is continued until the fermentation broth comprises at least 10 g/L natamycin, and the ratio of non-yeast protein component to yeast protein component is 5:1 to 7:1.

8. In a method for producing natamycin, comprising, in order, the steps of:

(a) introducing an inoculum of a natamycin producing Streptomyces strain to a fermentation medium to produce a fermentation broth comprising the fermentation medium and inoculum; and (b) producing natamycin by culturing the Streptomyces strain in the fermentation broth; the improvement comprising:

(1) providing at least about 15 g/L of a protein nitrogen source to the fermentation medium, wherein the protein nitrogen source comprises a non-yeast protein component and a yeast protein component, and the ratio of non-yeast protein component to yeast protein component being from about 3:1 to 9:1, based on the protein content of the source;

(2) providing a carbon source to the fermentation medium at from about 80 g/L to 250 g/L, wherein the carbon source addition is carried out during step (b) so as to maintain a concentration of carbon source of from about 5 g/L to 30 g/L;

(3) continuing the fermentation until the fermentation broth comprises at least 5 g/L natamycin; and (4) removing a portion of said fermentation broth and replacing said removed portion by adding a substantially equivalent amount of fresh fermentation medium.

9. The method of claim 8 in which said removing and said replacing of step (4) are continuous.

10. The method of claim 8 in which said removing and said replacing of step (4) are intermittent.

11. The method of claim 8, wherein said natamycin producing Streptomyces strain has all the identifying characteristics of *Streptomyces gilvosporeus* ATCC 13326, and in which step (3) is continued until the fermentation broth comprises at least 7 g/L natamycin.

12. The method of claim 8 in which the natamycin producing Streptomyces strain is a strain of *Streptomyces gilvosporeus*.

13. The method of claim 8 in which the ratio of non-yeast protein component to yeast protein component is 4:1 to 8:1.

14. The method of claim 8, in which the ratio of non-yeast protein component to yeast protein component is 5:1 to 7:1.

15. The method of claim 8 in which, in step (4), methanol is added, the pH adjusted to 1.0 to 4.5, solids removed, the pH raised to 6.0–9.0 and the precipitated natamycin recovered.

16. The method for producing natamycin according to claim 8, further comprising the step of recovering natamycin from the portion of said fermentation broth removed in step (4) of claim 8.

* * * * *